(12) United States Patent
Lin

(10) Patent No.: US 7,112,240 B2
(45) Date of Patent: Sep. 26, 2006

(54) STERILIZING AIR FILTER

(76) Inventor: Kun-Chang Lin, No. 1, Lane 201, Lienchih Rd., Lienmei Village, Tapi Hsiang, Yunlin Hsien (TW)

(*) Notice: Subject to any disclaimer, the term of this patent is extended or adjusted under 35 U.S.C. 154(b) by 405 days.

(21) Appl. No.: 10/782,842

(22) Filed: Feb. 23, 2004

(65) Prior Publication Data

US 2005/0257689 A1    Nov. 24, 2005

(51) Int. Cl.
*A61L 9/14*    (2006.01)
*B01D 53/18*    (2006.01)

(52) U.S. Cl. ............... 96/227; 96/297; 261/115; 422/122

(58) Field of Classification Search .......... 96/227, 96/243, 271, 272, 273, 296, 297, 326; 95/210; 261/100, 101, 103, 106, 115; 422/122
See application file for complete search history.

(56) References Cited

U.S. PATENT DOCUMENTS 2,095,539 A * 10/1937 Bichowsky ............ 261/98
2,234,735 A * 3/1941 Lambert et al. ............ 96/228
3,733,789 A * 5/1973 Rebours .................. 96/297
5,509,946 A * 4/1996 Chu ........................ 96/140
6,840,987 B1* 1/2005 Gonzalez et al. ............ 96/274
2003/0031588 A1* 2/2003 Schur ...................... 422/28

* cited by examiner

*Primary Examiner*—Frank M. Lawrence
(74) *Attorney, Agent, or Firm*—Lowe Hauptman & Berner

(57) ABSTRACT

A sterilizing air filter has a casing, a base, multiple spray devices, a cover, multiple fans and multiple bent tubes. The casing has an inlet and an outlet. The base is mounted in the casing and has multiple chambers in the base. Disinfectant can be poured into the chambers. The spray devices respectively mounted in the chambers and the cover fitted on the base are both used for spraying disinfectant in the chamber. The multiple fans and the multiple bent tubes are used for spreading the sprayed disinfectant between the different chambers and out to the air. The sterilizing air filter not only sucks the air into the microbial filter for sterilization and filtration but also automatically sprays the disinfectant out to the air to kill microbes in the air.

7 Claims, 5 Drawing Sheets

US 7,112,240 B2

STERILIZING AIR FILTER

BACKGROUND OF THE INVENTION

1. Field of the Invention

Figure 1:
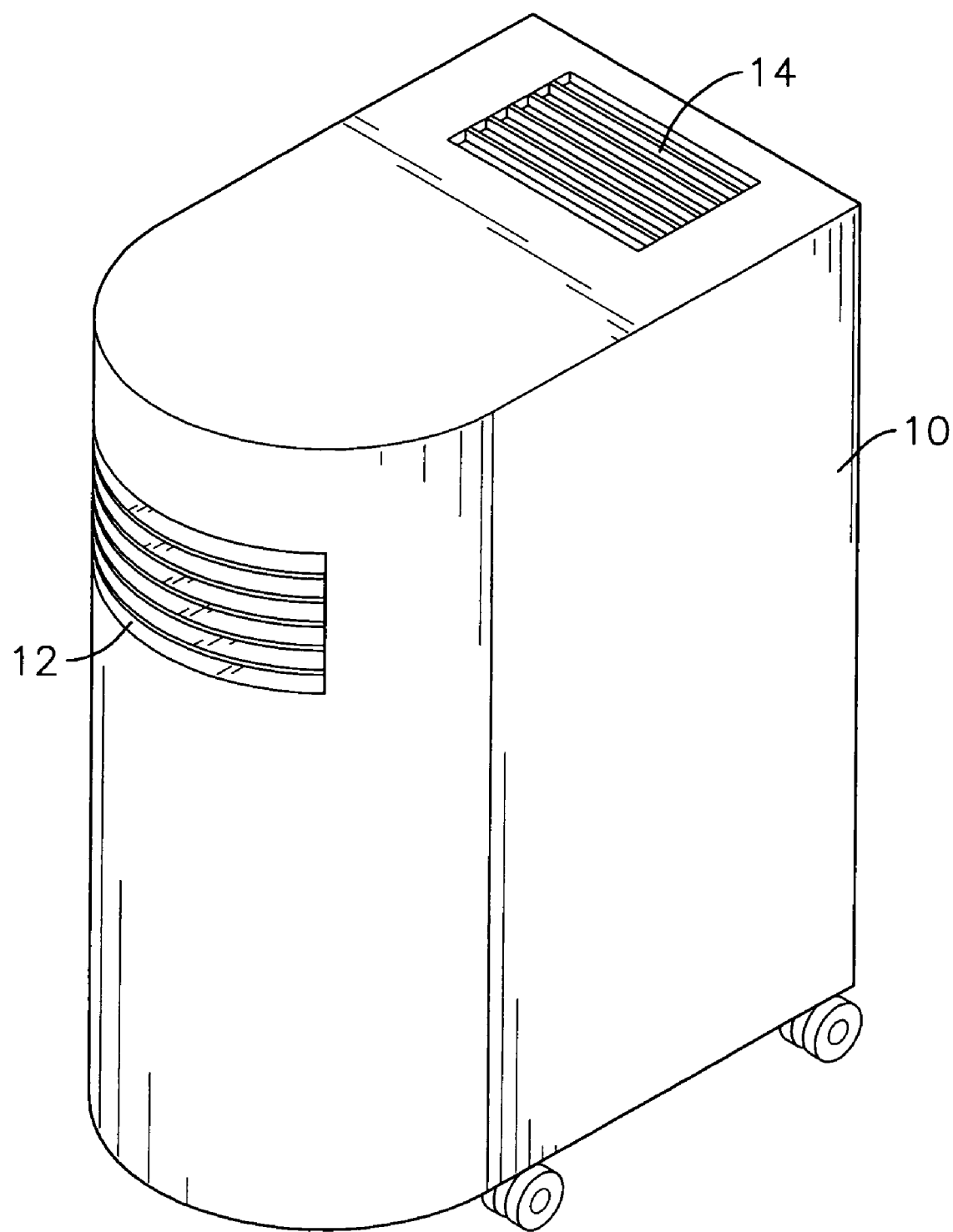
Figure 2:
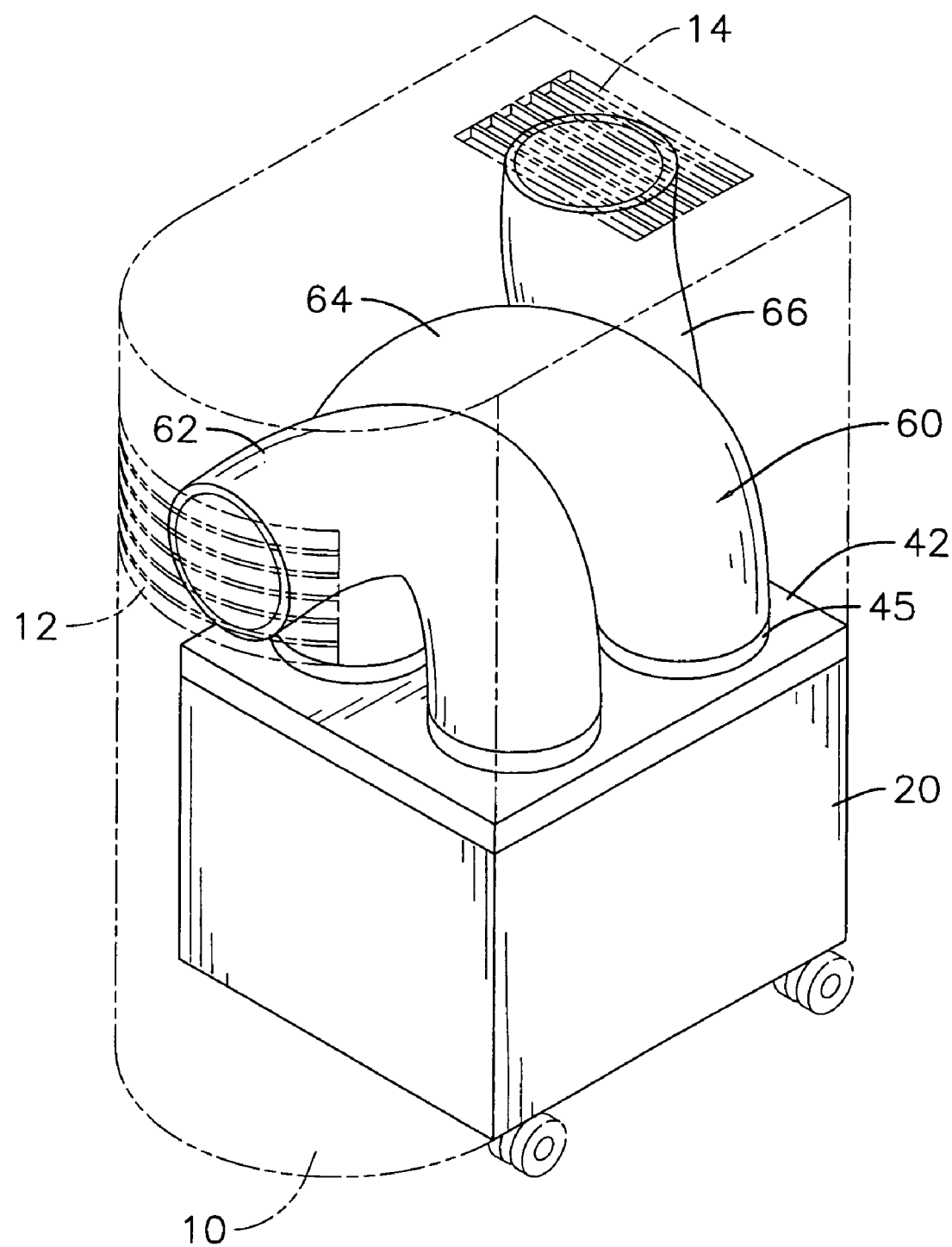
Figure 3:
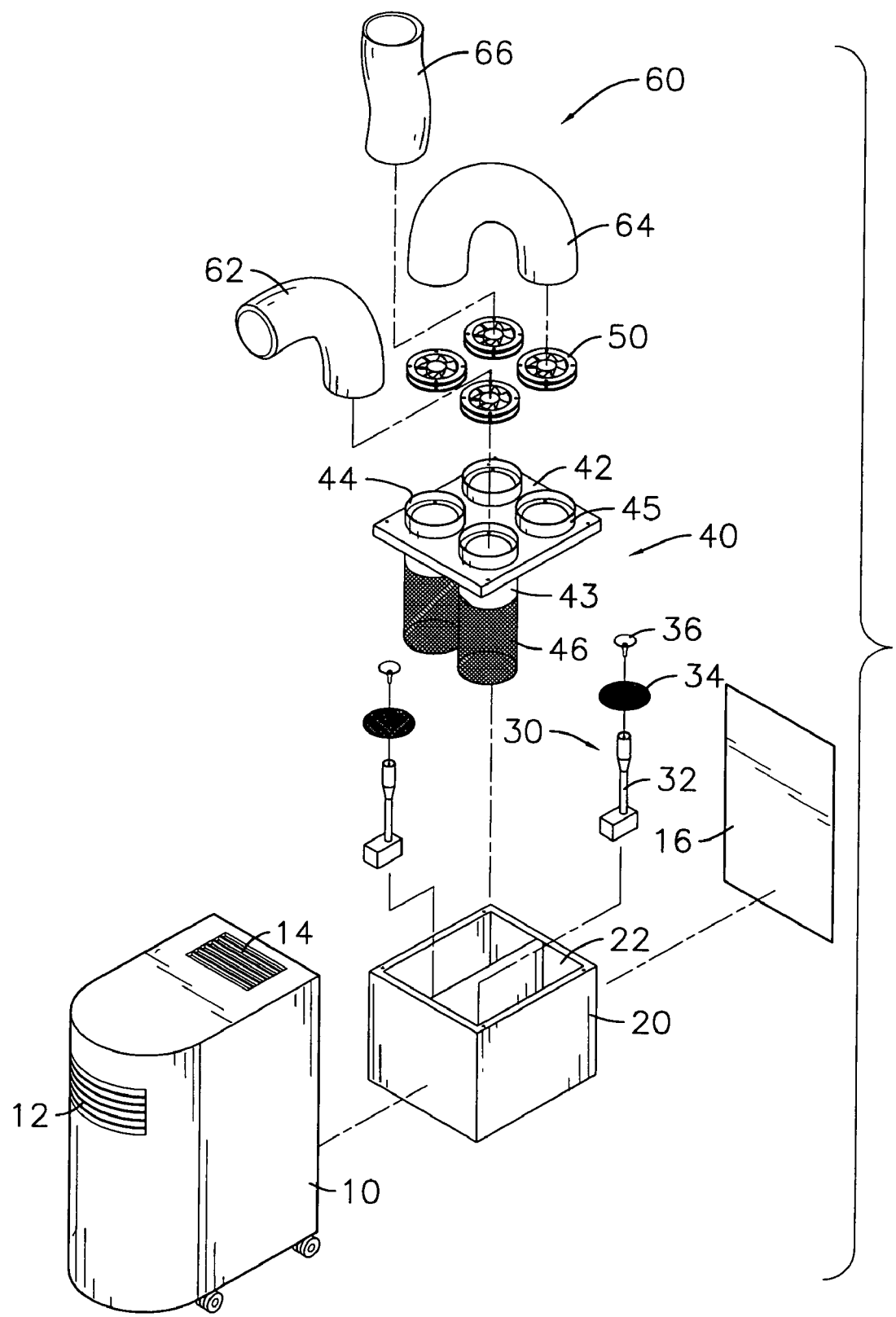

The present invention relates to an air filter, and more particularly to an air filter for sterilizing and filtering the air.

2. Description of Related Art

Some infecting microbes, e.g. influenza virus, corona virus, parainfluenza virus, are spread into the atmosphere by sneezing and vomiting of patients. When people are in enclosed spaces, healthy people may become infected through the ventilation system, such as an air conditioner unit. At this time, people must wear respirators for preventing such infection. If any method or device can sterilize or filter the air to eliminate the infected microbes, people may feel relieved that they do not need to wear respirators. A conventional method for sterilizing microbes is using 70% ethanol in a sprayer to sterilize the desired place, e.g. a table, hand or container. However, the sprayer must be manually operated and no automatic machine can filter the air as well as spray disinfectant to the air.

SUMMARY OF THE INVENTION

The main objective of the present invention is to provide an automatic sterilizing air filter that can sterilize and filtrate microbes and spray disinfectant in the air.

To achieve the objective, a sterilizing air filter in accordance with the present invention comprises a casing, a base, multiple spray devices, a cover, multiple fans and multiple bent tubes. The casing has an inlet and an outlet. The base is mounted in the casing and has multiple chambers in the base. The disinfectant can be poured into the chambers. The spray devices respectively mounted in the chambers and the cover fitted on the base are used for spraying disinfectant in the air of the chamber. The multiple fans are mounted in the cover and the multiple bent tubes are mounted with the cover and correspond to the inlet or the outlet in the casing for spreading the sprayed disinfectant between the different chambers and out to the air. The sterilizing air filter not only sucks the air into the sterilizing air filter for sterilization and filtration but also automatically sprays the disinfectant out to the air to kill microbes in the air.

Further benefits and advantages of the present invention will become apparent after a careful reading of the detailed description with appropriate reference to the accompanying drawings.

BRIEF DESCRIPTION OF THE DRAWINGS

FIG. 1 is a perspective view of a sterilizing air filter in accordance with the present invention;

FIG. 2 is a perspective view of an internal part of the sterilizing air filter in FIG. 1;

FIG. 3 is an exploded perspective view of the sterilizing air filter in FIG. 1

FIG. 4 is a top plane view of multiple tubes of the sterilizing air filter in FIG. 1; and FIG. 5 is a side plane view of the sterilizing air filter in FIG. 1.

DETAILED DESCRIPTION OF THE INVENTION

With reference to FIGS. 1 to 3, a sterilizing air filter in accordance with the present invention comprises a casing (10), a base (20), multiple spray devices (30), a cover (40), multiple fans (50) and multiple bending tubes (60).

The casing (10) has a top (not numbered), a bottom (not numbered), a sidewall (not numbered), an optional opening (not shown), an optional plate (16), an inlet (12) and an outlet (14). In a preferred embodiment, the inlet (12) is formed through the sidewall and the outlet (14) is formed through the top. The optional opening is formed in the sidewall and the plate (16) covers the opening.

The base (20) is mounted in the casing (10) and has multiple chambers (22) defined in the base (20). In a preferred embodiment of the present invention, the base (20) has two chambers (22) named first chamber (not numbered) and second chamber (not numbered).

The multiple spray devices (30) are respectively mounted in the chambers (22) and each has an electric pump (32), a flat filter (34) and an optional spray head (36). The electric pump (32) is mounted in the corresponding chamber (22) and has a top (not numbered). The flat filter (34) is mounted on the top of the electric pump (32). In a preferred embodiment of the present invention, the optional spray head (36) is mounted on the flat filter (34) and connected with the top of the electric pump (32). In a preferred embodiment of the present invention, the microbial filter has two spray devices (30) and one is mounted in the first chamber (22) and the other is mounted in the second chamber (22).

The cover (40) is fitted on the base (20) and has a plate (42), multiple holes (44), multiple connecting tubes (45), multiple optional setting tubes (43) and multiple tubular filters (46). The plate (42) is mounted on the base (20). The holes (44) are formed in the plate (42) and each has a periphery (not numbered). In a preferred embodiment of the present invention, the cover (40) has four holes (44). Two holes (44) are corresponded with the first chamber (22) of the base (20) and the other two holes (44) are corresponded with the second chamber (22) of the base (20). The multiple connecting tubes (45) are formed integrally and extend upward from the plate (42) and the periphery of the corresponding hole (44). The multiple tubular filters (46) each have a proximal end (not numbered) and a distal end (not numbered). The proximal end of the tubular filter (46) is connected around the periphery of the corresponding hole (44). The distal end of the tubular filter (46) is mounted around the corresponding spray device (30) in the chamber (22) of the base (20). In a preferred embodiment of the present invention, the tubular filters (46) are connected with one of the two holes corresponded with the same chamber (22) of the base (20). The optional setting tubes (43) are formed integrally with and extend downward from the plate (42) and the periphery of the corresponding holes (44). The multiple tubular filters (46) are preferably mounted around the corresponding setting tube (43).

The multiple fans (50) are respectively mounted in the connecting tubes (45).

The multiple bent tubes (60) are mounted with the connecting tubes (45) on the plate (42) of the cover (40) and correspond to the inlet (12) in the casing (10) or the outlet (14) in the casing (10). In a preferred embodiment of the present invention, the sterilizing air filter has three bent tubes (60) respectively named first bent tube (62), second bent tube (64) and third bent tube (66). The first bent tube (62) has a proximal end (not numbered) and a distal end (not numbered). The proximal end of the first bent tube (62) is connected with the connecting tube (45) that has the tubular filter (46) mounted corresponding to the first chamber (22) of the base (20). The distal end of the first bent tube (62) is mounted corresponding to the inlet (12) in the casing (10).

The second bent tube (64) has a proximal end (not numbered) and a distal end (not numbered). The proximal end of the second bent tube (64) is connected with the connecting tube (45) that has no tubular filter (46) mounted corresponding to the first chamber (22). The distal end of the second bent tube (64) is connected with the connecting tube (45) that has the tubular filter (46) mounted corresponding to the second chamber (22). The third bent tube (66) has a proximal end (not numbered) and a distal end (not numbered). The proximal end of the third bent tube (66) is connected with the connecting tube (45) that has no tubular filter (46) mounted corresponding to the second chamber (22). The distal end of the third bent tube (66) is mounted corresponding to the outlet (14) in the casing (10).

Figure 4:
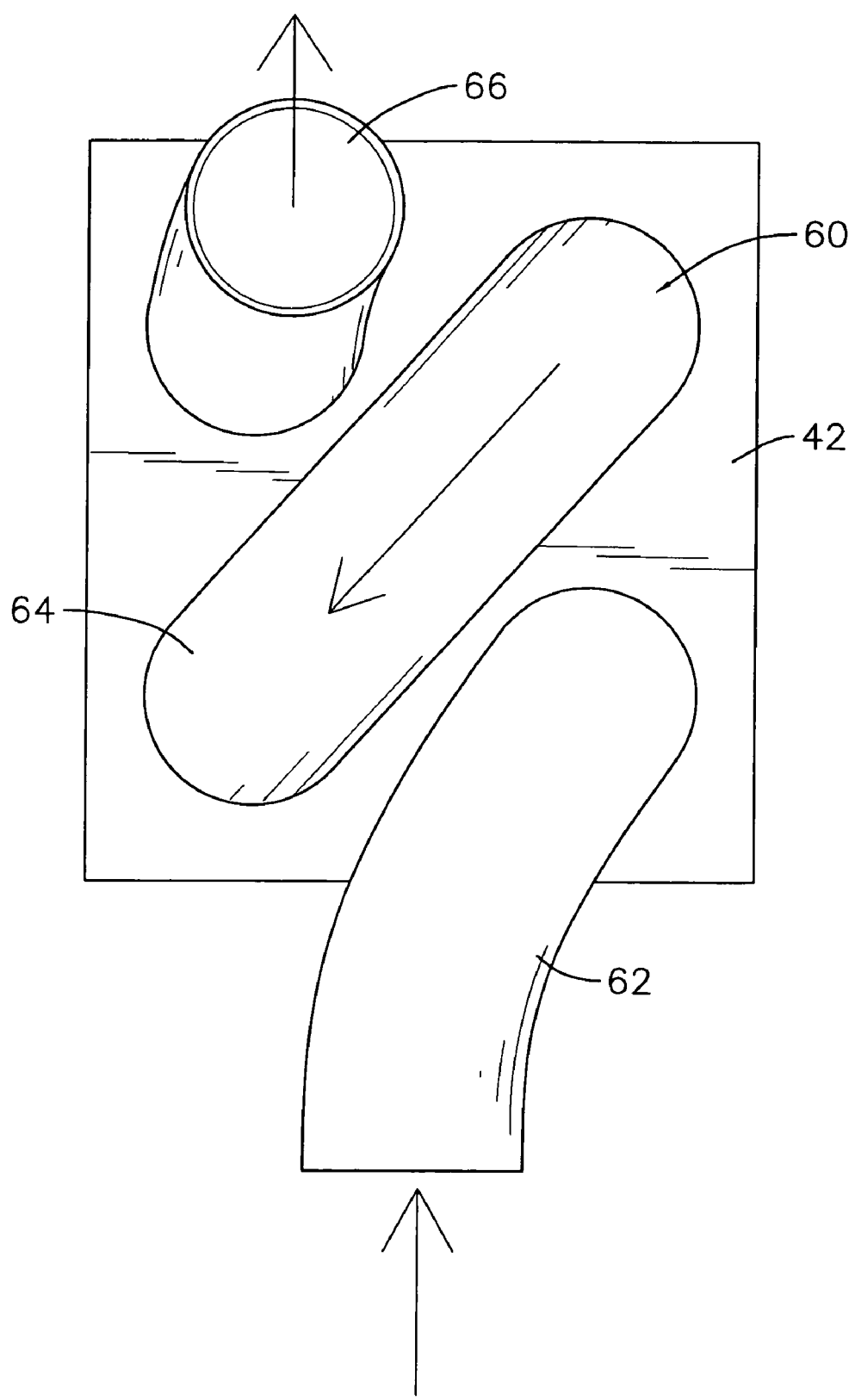
Figure 5:
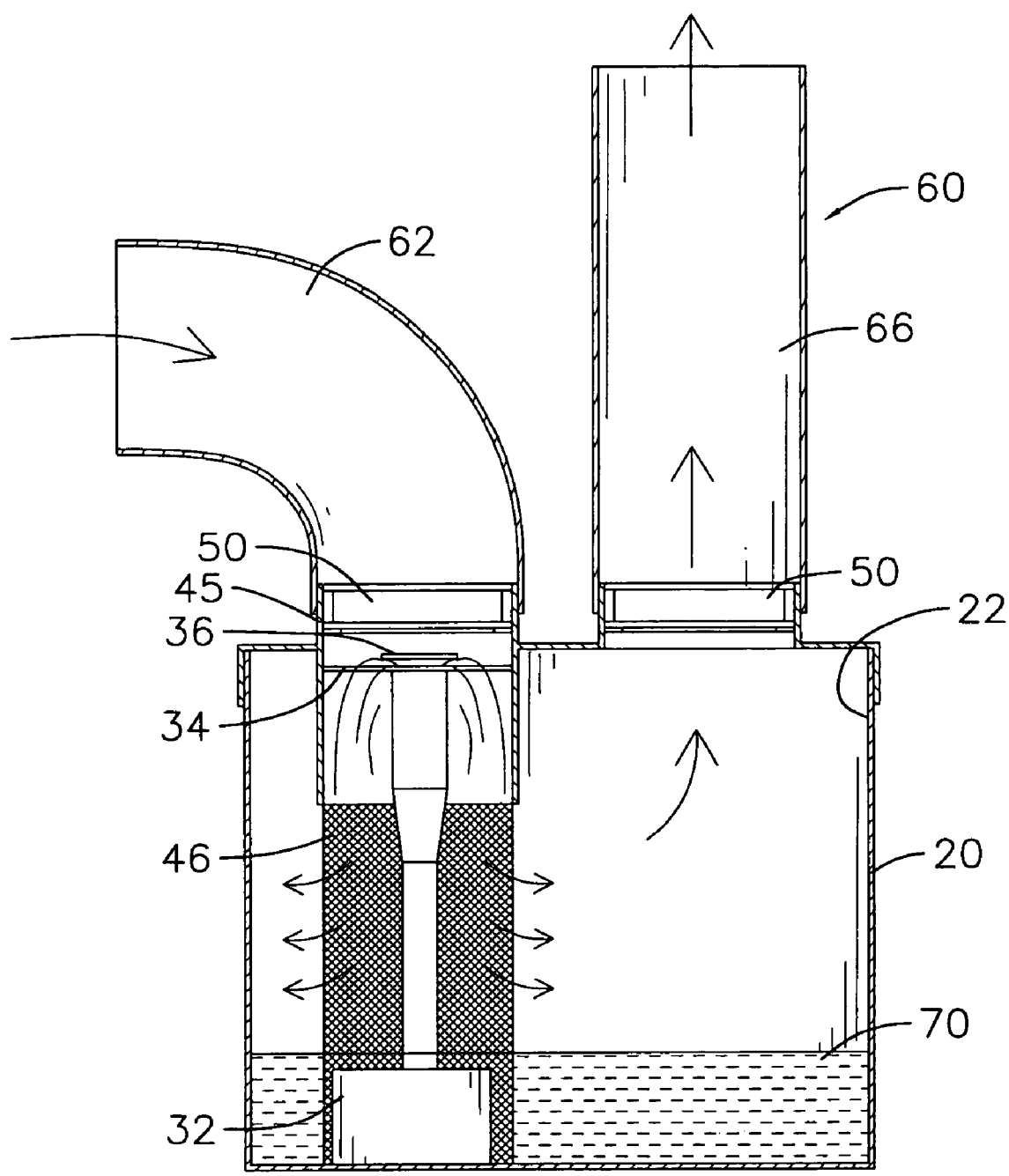

With further reference to FIGS. 4 to 5, the disinfectant that can be directed against specific microbes is poured into the base (20). The disinfectant is pumped upward by the electric pump (32) to the top of the electric pump (32) and preferably sprayed from the spray head (36) to the flat filter (34). The sprayed disinfectant flows down and through of the tubular filter (46). The fan (50) corresponded with the first bent tube (62) lets the air flow from the inlet (12) in the casing (10) and blows the sprayed disinfectant through of the flat filter (34) and the tubular filter (46). The fan (50) corresponded with the second bent tube (64) lets the air with the sprayed disinfectant flow out to the second chamber (22) of the base (20). The electric pump (32) in the second chamber (22) also pumps the disinfectant to the flat filter (34) and the tubular filter (46). The fan (50) connected correspondingly to the distal end of the second bent tube (64) lets the air with the sprayed disinfectant in the first chamber (22) blow the disinfectant through of the flat filter (34) and the tubular filter (46) in the second chamber (22) to spray the disinfectant. The fan (50) connected corresponding to the proximal end of the third bent tube (66) lets the air with the sprayed disinfectant flow out from the outlet (14) in the casing (10).

The sterilizing air filter not only sucks the air into the microbial filter for sterilization and filtration but also automatically sprays the disinfectant out to the air to kill microbes in the air.

Although the invention has been explained in relation to its preferred embodiment, many other possible modifications and variations can be made without departing from the spirit and scope of the invention as hereinafter claimed.

What is claimed is:

1. A sterilizing air filter comprising:

a casing having a top;

a bottom;

a sidewall;

an inlet formed in the casing; and an outlet formed in the casing;

a base mounted in the casing and having multiple chambers defined in the base;

multiple spray devices respectively mounted in the chambers and each having an electric pump mounted in a corresponding chamber and having a top; and a flat filter mounted on the top of the electric pump;

a cover mounted on the base and having a plate covering the base;

multiple holes formed in the plate and each multiple hole having a periphery;

multiple connecting tubes formed integrally and extended upward from the plate and respectively around the peripheries of the holes; and multiple tubular filters each having a proximal end and a distal end, wherein the proximal end of each tubular filter is connected around the periphery of a corresponding hole and the distal end of each tubular filter is mounted around one of the spray devices in the chamber of the base;

multiple fans respectively mounted in the connecting tubes; and multiple bent tubes respectively mounted with the connecting tubes on the plate of the cover and two of the bent tubes corresponding to the inlet in the casing and the outlet in the casing.

2. The sterilizing air filter as claimed in claim 1, wherein the inlet is formed through the sidewall of the casing and the outlet is formed through the top of the casing.

3. The sterilizing air filter as claimed in claim 2, wherein the base has two chambers named first chamber and second chamber;

the sterilizing air filter has two spray devices and one is mounted in the first chamber and the other is mounted in the second chamber; and the cover has four holes, two holes are corresponded with the first chamber of the base and the other two holes are corresponded with the second chamber of the base and two tubular filters are respectively connected with two of the holes that are corresponded respectively with the first and second chambers of the base.

4. The sterilizing air filter as claimed in claim 3, wherein the sterilizing air filter has three bent tubes are respectively named first bent tube, second bent tube and third bent tube;

the first bent tube has a proximal end and a distal end and the proximal end of the first bent tube is connected with the connecting tube that has the tubular filter mounted corresponding to the first chamber of the base and the distal end of the first bent tube is mounted corresponding to the inlet in the casing;

the second bent tube has a proximal end and a distal end and the proximal end of the second bent tube is connected with the connecting tube without a tubular filter mounted corresponding to the first chamber and the distal end of the second bent tube is connected with the connecting tube that has the tubular filter mounted corresponding to the second chamber; and the third bent tube has a proximal end and a distal end and the proximal end of the third bent tube is connected with the connecting tube without a tubular filter mounted corresponding to the second chamber and the distal end of the third bent tube is mounted corresponding to the outlet in the casing.

5. The sterilizing air filter as claimed in claim 4, wherein each spray device further comprises a spray head mounted on the flat filter and connected with the top of the electric pump.

6. The sterilizing air filter as claimed in claim 5, wherein the cover further comprises multiple setting tubes formed integrally with and extended downward from the plate and the peripheries of the holes and the tubular filters are respectively mounted around the setting tubes.

7. The sterilizing air filter as claimed in claim 6, wherein the casing further comprises an opening formed in the sidewall and a plate covers the opening.

* * * * *